United States Patent
Font Freide et al.

(10) Patent No.: US 7,012,102 B2
(45) Date of Patent: Mar. 14, 2006

(54) FISCHER-TROPSCH PROCESS

(75) Inventors: Josephus Johannes Helena Maria Font Freide, Guildford (GB); Stephen Anthony Leng, Ashford (GB); Christopher Sharp, Beverley (GB)

(73) Assignees: BP Exploration Operating Company Limited, London (GB); Davy Process Technology Limited, London (GB)

( * ) Notice: Subject to any disclaimer, the term of this patent is extended or adjusted under 35 U.S.C. 154(b) by 159 days.

(21) Appl. No.: 10/476,797

(22) PCT Filed: May 17, 2002

(86) PCT No.: PCT/GB02/02310

§ 371 (c)(1),
(2), (4) Date: Nov. 6, 2003

(87) PCT Pub. No.: WO02/096839

PCT Pub. Date: Dec. 5, 2002

(65) Prior Publication Data

US 2004/0132837 A1    Jul. 8, 2004

(30) Foreign Application Priority Data

May 25, 2001    (GB)    .................................... 0112796

(51) Int. Cl.
*C07C 27/00*    (2006.01)
*C07C 1/00*    (2006.01)
(52) U.S. Cl. ....................... 518/700; 518/705; 518/715; 585/315

(58) Field of Classification Search ................ 518/700, 518/705, 715; 585/315
See application file for complete search history.

(56) References Cited

U.S. PATENT DOCUMENTS

| 4,754,092 A | * | 6/1988 | Iglesia et al. ................ 585/469 |
| 5,939,350 A | | 8/1999 | Singleton et al. |
| 5,961,933 A | | 10/1999 | Casanave et al. |

FOREIGN PATENT DOCUMENTS

| EP | 0 261 870 A | 3/1988 |
| EP | 0 522 666 A | 1/1993 |
| GB | 2 037 316 A | 7/1980 |
| WO | WO 93 15835 A | 8/1993 |
| WO | WO 01/38269 A1 * | 5/2001 |

* cited by examiner

*Primary Examiner*—J. Parsa
(74) *Attorney, Agent, or Firm*—Nixon & Vanderhye

(57) ABSTRACT

The present invention provides a process for the conversion of synthesis gas to hydrocarbons comprising the steps of: a) contacting synthesis gas at an elevated temperature and pressure with a particulate Fischer-Tropsch catalyst in a Fischer-Tropsch reactor system to generate hydrocarbons comprising gaseous and liquid hydrocarbons; b) in a gas separation zone, separating a gaseous phase comprising saturated gaseous hydrocarbons from a liquid phase comprising liquid hydrocarbons and from the particulate Fischer-Tropsch catalyst; c) passing at least a portion of the separated gaseous phase to a dehydrogenation reactor where at least a portion of the saturated gaseous hydrocarbons are converted to unsaturated hydrocarbons; and d) recycling at least a portion of said unsaturated hydrocarbons back to the Fischer-Tropsch reactor system.

15 Claims, 1 Drawing Sheet

FISCHER-TROPSCH PROCESS

This application is the U.S. National Phase of International Application PCT/GB02/02310, filed 17 May 2002, which designated the U.S.

FIELD OF THE INVENTION

The present invention relates to a process for the conversion of carbon monoxide and hydrogen (synthesis gas) to hydrocarbon products in the presence of a particulate catalyst. In the Fischer-Tropsch reaction synthesis gas is reacted in the presence of a heterogeneous catalyst to give a hydrocarbon mixture having a relatively broad molecular weight distribution. This product comprises predominantly straight chain saturated hydrocarbons which typically have a chain length of more than 5 carbon atoms. The Fischer-Tropsch reaction is highly exothermic.

SUMMARY OF THE INVENTION

It has now been found it is possible to promote hydrocarbon chain growth in a Fischer-Tropsch reactor by adding unsaturated hydrocarbons to the reactor. Consequently, a Fischer-Tropsch process can be integrated with a dehydrogenation process wherein a gaseous stream comprising saturated hydrocarbons from a Fischer-Tropsch reactor is withdrawn and passed into a dehydrogenation reactor and the product therefrom is at least in part passed back to the Fischer-Tropsch reactor. Advantageously the heat generated from the Fischer-Tropsch reaction can be used to supply heat to the dehydrogenation reactor.

Accordingly the present invention provides a process for the conversion of synthesis gas to hydrocarbons comprising the steps of:
a) contacting synthesis gas at an elevated temperature and pressure with a particulate Fischer-Tropsch catalyst in a Fischer-Tropsch reactor system to generate hydrocarbons comprising gaseous and liquid hydrocarbons;
b) in a gas separation zone, separating a gaseous phase comprising saturated gaseous hydrocarbons from a liquid phase comprising liquid hydrocarbons and from the particulate Fischer-Tropsch catalyst;
c) passing at least a portion of the separated gaseous phase to a dehydrogenation reactor where at least a portion of the saturated gaseous hydrocarbons are converted to unsaturated hydrocarbons; and
d) recycling at least a portion of said unsaturated hydrocarbons back to the Fischer-Tropsch reactor.

Preferably a stream comprising ethane, propane and butane is fed to the dehydrogenation reactor in addition to the separated gaseous phase.

The synthesis gas may be contacted with the particulate Fischer-Tropsch catalyst in a fixed or fluidized bed reactor but, preferably, in a slurry reactor e.g. a slurry bubble column in which a Fischer-Tropsch catalyst is primarily distributed and suspended in the slurry by the energy imparted from the synthesis gas rising from the gas distribution means at the bottom of the slurry bubble column as described in, for example, U.S. Pat. No. 5,252,613.

The synthesis gas may also be contacted with a suspension of a particulate Fischer-Tropsch catalyst in a liquid medium in a system comprising at least one high shear mixing zone and a reactor vessel such as the Fischer-Tropsch process described in WO 0138269 (PCT patent application number GB 0004444) which is herein incorporated by reference.

Accordingly, a preferred embodiment of the invention provides a process which comprises contacting the gaseous reactant stream comprising synthesis gas at elevated temperature and pressure with a suspension of a particulate Fischer-Tropsch catalyst in a liquid medium in a reactor system comprising at least one high shear mixing zone and a reactor vessel wherein the process comprises:
(a) passing the suspension through the high shear mixing zone(s) where the synthesis gas is mixed with the suspension;
(b) discharging a mixture comprising the synthesis gas and the suspension from the high shear mixing zone(s) into the reactor vessel;
(c) in the reactor vessel, converting the synthesis gas to hydrocarbons comprising gaseous and liquid hydrocarbons to form a product suspension comprising the catalyst suspended in the liquid medium and the liquid hydrocarbons;
(d) in a gas separation zone, separating a gaseous phase comprising saturated gaseous hydrocarbons from the product suspension;
(e) passing at least a portion of said separated gaseous phase to a dehydrogenation reactor where at least a portion of the saturated gaseous hydrocarbons are converted to unsaturated hydrocarbons; and
(f) recycling at least a portion of said unsaturated hydrocarbons back to the Fischer-Tropsch reactor system.

The synthesis gas used in the process of the present invention may be prepared using any of the processes known in the art including partial oxidation of hydrocarbons, steam reforming, gas heated reforming, microchannel reforming (as described in, for example, U.S. Pat. No. 6,284,217 which is herein incorporated by reference), plasma reforming, autothermal reforming and any combination thereof. A discussion of these synthesis gas production technologies is provided in "Hydrocarbon Processing" V78, N.4, 87–90, 92–93 (April 1999) and "Petrole et Techniques", N. 415, 86–93 (July–August 1998). It is also envisaged that the synthesis gas may be obtained by catalytic partial oxidation of hydrocarbons in a microstructured reactor as exemplified in "IMRET 3: Proceedings of the Third International Conference on Microreaction Technology", Editor W Ehrfeld, Springer Verlag, 1999, pages 187–196. Alternatively, the synthesis gas maybe obtained by short contact time catalytic partial oxidation of hydrocarbonaceous feedstocks as described in EP 0303438. Preferably, the synthesis gas is obtained via a "Compact Reformer" process as described in "Hydrocarbon Engineering", 2000, 5, (5), 67–69; "Hydrocarbon Processing", 79/9, 34 (September 2000); "Today's Refinery", 15/8, 9 (August 2000); WO 99/02254; and WO 200023689. These synthesis gas production technologies are hereinafter referred to as the "synthesis gas production stage" Preferably a natural gas stream comprising methane is passed to the synthesis gas production stage which produces the synthesis gas used in the Fischer-Tropsch process as herein described above.

In a preferred embodiment, the process comprises using the heat generated in the Fischer-Tropsch reactor system (exothermic heat of reaction) to heat the contents of the dehydrogenation reactor. Thus, the Fischer-Tropsch reactor system may comprise at least one internal heat exchanger where coolant liquid is fed to the heat exchanger to remove exothermic heat of reaction from the system. The heat removed by the coolant liquid may then be used to increase the temperature of the dehydrogenation reactor.

The Fischer-Tropsch reactor system may also have an external heat exchanger for cooling a recycle stream which is withdrawn from the reactor system. The heat removed by the coolant liquid which is fed to the external heat exchanger may then be used to increase the temperature of the dehydrogenation reactor.

Alternatively at least a portion of the stream comprising ethane, propane and butane which is fed to the dehydrogenation reactor may be combusted to generate heat energy to increase the temperature within the dehydrogenation reactor. Generally both sources of heat energy may be used in combination.

Where the Fischer-Tropsch reactor system comprises at least one high shear mixing zone and a reactor vessel, the reactor vessel may be a tank reactor or a tubular loop reactor.

The high shear mixing zone(s) may be part of the reactor system inside or outside the reactor vessel, for example, the high shear mixing zone(s) may project through the walls of the reactor vessel such that the high shear mixing zone(s) discharges its contents into the reactor vessel. Preferably, the reactor system comprises up to 250 high shear mixing zones, more preferably less than 100, most preferably less than 50, for example 10 to 50 high shear mixing zones. Preferably, the high shear mixing zones discharge into or are located within a single reactor vessel as described in WO 0138269 (PCT patent application number GB 0004444). It is also envisaged that 2 or 3 such reactor systems may be employed in series.

Suitably, the volume of suspension present in the high shear mixing zone(s) is substantially less than the volume of suspension present in the reactor vessel, for example, less than 20%, preferably less than 10% of the volume of suspension present in the reactor vessel.

The high shear mixing zone(s) may comprise any device suitable for intensive mixing or dispersing of a gaseous stream in a suspension of solids in a liquid medium, for example, a rotor-stator device, an injector-mixing nozzle or a high shear pumping means, but is preferably an injector mixing nozzle(s). Suitably, the device is capable of breaking down the gaseous stream into gas bubbles and/or irregularly shaped gas voids.

The kinetic energy dissipation rate in the high shear mixing zone(s) is suitably, at least 0.5 kW/m$^3$ relative to the total volume of suspension present in the system, preferably in the range 0.5 to 25 kW/m$^3$, more preferably 0.5 to 10 kW/m$^3$, most preferably 0.5 to 5 kW/m$^3$, and in particular, 0.5 to 2.5 kW/m$^3$ relative to the total volume of suspension present in the system.

Where the high shear mixing zone(s) comprise an injector-mixing nozzle(s) the injector-mixing nozzle(s) can advantageously be executed as a venturi tube (c.f. "Chemical Engineers' Handbook" by J. H. Perry, 3$^{rd}$ edition (1953), p. 1285, FIG. 61), preferably an injector mixer (c.f. "Chemical Engineers' Handbook" by J. H. Perry, 3$^{rd}$ edition (1953), p 1203, FIG. 2 and "Chemical Engineers' Handbook" by R H Perry and C H Chilton 5$^{th}$ edition (1973) p 6–15, FIGS. 6–31) or most preferably as a liquid-jet ejector (c.f. "Unit Operations" by G G Brown et al, 4$^{th}$ edition (1953), p. 194, FIG. 210). The injector mixing nozzle(s) may also be executed as a venturi plate positioned within an open ended conduit which discharges the mixture of synthesis gas and suspension into a tank reactor. Alternatively the venturi plate may be positioned within a tubular loop reactor. Suitably, synthesis gas is introduced into the open-ended conduit or tubular loop reactor downstream of the venturi plate. The injector-mixing nozzle(s) may also be executed as "gas blast" or "gas assist" nozzles where gas expansion is used to drive the nozzle (c.f. "Atomisation and Sprays" by Arthur H Lefebvre, Hemisphere Publishing Corporation, 1989).

Where the injector-mixing nozzle(s) is executed as a "gas blast" or "gas assist" nozzle, the suspension of catalyst is fed to the nozzle at a sufficiently high pressure to allow the suspension to pass through the nozzle while the gaseous reactant stream is fed to the nozzle at a sufficiently high pressure to achieve high shear mixing within the nozzle.

The high shear mixing zone(s) may also comprise a high shear pumping means, for example, a paddle or propeller having high shear blades positioned within an open ended pipe which discharges the mixture of synthesis gas and suspension into the reactor vessel. Preferably, the high shear pumping means is located at or near the open end of the pipe, for example, within 1 meter preferably within 0.5 metres of the open end of the pipe. Alternatively, the high shear pumping means may be positioned within a tubular loop reactor vessel. Synthesis gas may be injected into the pipe or tubular loop reactor vessel, for example, via a sparger, located immediately upstream or downstream, preferably upstream of the high shear pumping means, for example, preferably, within 1 meter, preferably within 0.5 meter of the high shear pumping means. Without wishing to be bound by any theory, the injected synthesis gas is broken down into gas bubbles and/or irregularly shaped gas voids by the fluid shear imparted to the suspension by the high shear pumping means.

Where the injector mixing nozzle(s) is executed as a venturi nozzle(s) (either a conventional venturi nozzle or as a venturi plate), the pressure drop of the suspension over the venturi nozzle(s) is typically in the range of from 1 to 40 bar, preferably 2 to 15 bar, more preferably 3 to 7 bar, most preferably 3 to 4 bar. Preferably, the ratio of the volume of gas ($Q_g$) to the volume of liquid ($Q_l$) passing through the venturi nozzle(s) is in the range 0.5:1 to 10:1, more preferably 1:1 to 5:1, most preferably 1:1 to 2.5:1, for example, 1:1 to 1.5:1 (where the ratio of the volume of gas ($Q_g$) to the volume of liquid ($Q_l$) is determined at the desired reaction temperature and pressure).

Where the injector mixing nozzle(s) is executed as a gas blast or gas assist nozzle(s), the pressure drop of gas over the nozzle(s) is preferably in the range 3 to 100 bar and the pressure drop of suspension over the nozzle(s) is preferably in the range of from 1 to 40 bar, preferably 4 to 15, most preferably 4 to 7. Preferably, the ratio of the volume of gas ($Q_g$) to the volume of liquid ($Q_l$) passing through the gas blast or gas assist nozzle(s) is in the range 0.5:1 to 50:1, preferably 1:1 to 10:1 (where the ratio of the volume of gas ($Q_g$) to the volume of liquid ($Q_l$) is determined at the desired reaction temperature and pressure).

Suitably, the shearing forces exerted on the suspension in the high shear mixing zone(s) are sufficiently high that the synthesis gas is broken down into gas bubbles having diameters in the range of from 1 $\mu$m to 10 mm, preferably from 30 $\mu$m to 3000 $\mu$m, more preferably from 30 $\mu$m to 300 $\mu$m.

Without wishing to be bound by any theory, it is believed that the irregularly shaped gas voids are transient in that they are coalescing and fragmenting on a time scale of up to 500 ms, for example, over a 10 to 50 ms time scale. The irregularly shaped gas voids have a wide size distribution with smaller gas voids having an average diameter of 1 to 2 mm and larger gas voids having an average diameter of 10 to 15 mm.

The high shear mixing zone(s) can be placed at any position on the walls of the reactor vessel (for example, at the top, bottom or side walls of a tank reactor). Where the reactor vessel is a tank reactor the suspension is preferably withdrawn from the reactor vessel and is at least in part recycled to a high shear mixing zone(s) through an external conduit having a first end in communication with an outlet for suspension in the reactor vessel and a second end in communication with an inlet of the high shear mixing zone. The suspension may be recycled to the high shear mixing zone(s) via a pumping means, for example, a slurry pump, positioned in the external conduit. Owing to the exothermic nature of the Fischer-Tropsch synthesis reaction, the suspension recycle stream is preferably cooled by means of a heat exchanger positioned on the external conduit (external heat exchanger). Additional cooling may be provided by means of an internal heat exchanger comprising cooling coils positioned within the suspension in the tank reactor. Preferably coolant liquid is fed to the heat exchanger(s) to remove exothermic heat of reaction from the system and the heat removed by the coolant liquid may then be used to increase the temperature of the dehydrogenation reactor.

Suitably, the ratio of the volume of the external conduit (excluding the volume of any external heat exchanger) to the volume of the tank reactor is in the range of 0.005:1 to 0.2:1.

Where the reactor vessel is a tubular loop reactor, a single high shear mixing zone, in particular an injector-mixing nozzle may discharge the mixture comprising synthesis gas and the suspension into the tubular loop reactor. Alternatively, a series of injector-mixing nozzles may be arranged around the tubular loop reactor. If necessary, suspension may be circulated around the tubular loop reactor via at least one mechanical pumping means e.g. a paddle or propeller. An external heat exchanger may be disposed along at least part of the tubular loop reactor, preferably along substantially the entire length of the tubular loop reactor thereby providing temperature control. It is also envisaged that an internal heat exchanger, for example cooling coils, tubes or plates may be located in at least part of the tubular loop reactor. The coolant liquid which is fed to the heat exchanger (s) to remove heat from the system may then be used to increase the temperature of the dehydrogenation reactor.

Preferably the Fischer-Tropsch reactor system of the preferred embodiment is operated with a gas hourly space velocity (GHSV) in the range of 100 to 40000 $h^{-1}$, more preferably 1000 to 30000 $h^{-1}$, most preferably 2000 to 15000, for example 4000 to 10000 $h^{-1}$ at normal temperature and pressure (NTP) based on the feed volume of synthesis gas at NTP.

The Fischer-Tropsch reaction is preferably carried out at a temperature of 180–280° C., more preferably 190–240° C. and preferably at a pressure of 5–50 bar, more preferably 15–35 bar, generally 20–30 bar.

The particulate Fischer-Tropsch catalyst comprises any particulate catalyst known to be active in Fischer-Tropsch synthesis and usually comprises supported or unsupported Group VIII metals. Of these iron, cobalt and ruthenium are preferred, particularly iron and cobalt, most particularly cobalt.

A preferred catalyst is supported on an inorganic oxide. Preferred supports include silica, alumina, silica-alumina, the Group IVB oxides, titania (primarily in the rutile form) and most preferably zinc oxide. The supports generally have a surface area of less than about 100 $m^2/g$, preferably less than 50 $m^2/g$, more preferably less than 25 $m^2/g$, for example, about 5 $m^2/g$.

The catalytic metal is present in catalytically active amounts usually about 1–100 wt %, the upper limit being attained in the case of iron based catalysts, preferably 2–40 wt %. Promoters may be added to the catalyst and are well known in the Fischer-Trospch catalyst art. Promoters can include aluminium, ruthenium, platinum or palladium (when not the primary catalyst metal), rhenium, hafnium, cerium, lanthanum and zirconium, and are usually present in amounts less than the primary catalytic metal (except for ruthenium which may be present in coequal amounts), but the promoter:metal ratio should be at least 1:10. Preferred promoters are rhenium and hafnium.

Preferably the particulate Fischer-Tropsch catalyst may have an average particle size in the range 5 to 500 microns, preferably 5 to 100 microns, for example, in the range 5 to 40 microns. Usually the suspension discharged into the reactor vessel comprises less than 40% by weight of catalyst, more preferably 10 to 30% by weight of catalyst, most preferably 10 to 20% by weight of catalyst.

Usually the liquid hydrocarbons produced by the Fischer-Tropsch synthesis reaction comprise a mixture of saturated hydrocarbons having a chain length of greater than 5 carbon atoms. Suitably, the liquid hydrocarbons comprise a mixture of saturated hydrocarbons having chain lengths of from 5 to about 90 carbon atoms. Preferably, a major amount, for example, greater than 60% by weight, of the saturated hydrocarbons have chain lengths of from 5 to 30 carbon atoms. Suitably, the liquid medium comprises one or more of the liquid hydrocarbons produced by the Fischer-Tropsch synthesis reaction.

The separated gaseous phase may comprise vaporized low boiling liquid hydrocarbon products, and gaseous hydrocarbons having from 1 to 3 carbon atoms such as methane, ethane and propane, in addition to unconverted synthesis gas and carbon dioxide. Preferably at least part of the gaseous phase is recycled to Fischer-Tropsch reactor system and at least part of the gaseous phase is passed to the dehydrogenation reactor.

Preferably, the dehydrogenation reaction is operated with a gas hourly space velocity (GHSV) in the range of 0.1 to 100 $h^{-1}$, more preferably 1 to 50 $h^{-1}$, most preferably 20 to 40 $h^{-1}$ at normal temperature and pressure (NTP) based on the feed volume of gaseous stream at NTP.

The dehydrogenation process may be performed at elevated temperature e.g. 100–900° C. such as 200–800° C. such as 300–700° C. The pressure may be 0.1–10 bar such as 1–5 or 2–4 bar.

In a preferred embodiment of the invention the dehydrogenation reactor comprises a dehydrogenation catalyst.

The dehydrogenation catalyst may be any suitable dehydrogenation catalyst well known to the person skilled in the art. The dehydrogenation catalyst usually comprises at least one elemental metal and a support wherein said metal is selected from Group IVA, VA, VIA, VIIA, VIII, IB, and IIB. The groups are as described in the Periodic Table in Advanced Inorganic Chemistry by F. A. Cotton and G. Wilkinson Publ. Interscience New York 2nd Ed. 1966. The metal is usually selected from Group VIII, IB, and IIB e.g. copper, silver and gold, preferably VIII e.g. iron, nickel and cobalt and most preferably from the platinum group metals including ruthenium, rhodium, palladium, osmium, iridium and platinum in particular platinum and palladium.

The metals may be deposited upon any suitable support with a sufficiently high surface area. The support may be amorphous or may possess a crystalline structure or contain both amorphous and crystalline portions. The supports usually have average surface areas of 20–1000 $m^2/g$, in particular 50–800 $m^2/g$ and especially 100–400 $m^2/g$ e.g. 300 $m^2/g$ (measured by BET method).

The support is usually a solid metal oxide or solid non metal oxide, each with surface OH groups. Examples of such metal oxides are those from tri and tetravalent metals which may be transition or non transition metals or any rare earth such as alumina, titania, cobaltic oxide, zirconia, ceria, molybdenum oxide and tungsten oxide and an example of such a non metal oxide is silica. Alternatively activated carbon, coke, or charcoal may provide suitable supports.

The support may also be a zeolite or zeotype material having a structure made up of tetrahedra joined together through oxygen atoms to produce an extended network with channels of molecular dimensions. The zeolite/zeotype materials have SiOH and/or Al—OH groups on the external or internal surfaces.

Advantageously the support comprises at least one of alumina, silica, silicalite, ceria and titania in particular silica or silicalite.

The metals may be deposited upon a support by any of the well known methods of catalyst preparation in particular impregnation wherein the pores of the support are filled at least partly with a salt of the particular metal in solution and the catalyst is subsequently dried, and optionally calcined and then the metal is reduced to be in elemental form. Alternatively surface hydroxyl groups of an acidic oxide support can be employed by exchange in aqueous solution of protons for other cations. The hydroxyl groups of a basic oxide support can be exchanged for other metal containing anions; again the support may then be dried, and if desired calcined and then optionally reduced. In a further embodiment of the invention metals ions may be ion exchanged with the cations present within the structure of the support.

Alternatively the dehydrogenation catalyst may be prepared by co-precipitation which comprises contacting a base e.g. ammonium bicarbonate, with a solution of salts of the metal and intended support e.g. nickel(II)nitrate and aluminium nitrate. A precipitate containing the mixed hydroxides is formed and after washing, drying and calcination a mixture of oxides is formed e.g. nickel(II) oxide and alumina. Subsequent reduction with hydrogen produces an elemental catalyst e.g. nickel/alumina.

The dehydrogenation catalysts comprise at least one second metal. The second metal is preferably chosen from a different group of the Periodic Table from the first metal, which is especially of Group VIII, while the second metal is especially at least one of Group VIA, VIIA, IB, IIB, IVB or VB, in particular in combination with the Group VIII metal. The second metal is preferably at least one of zinc, rhenium, tin, molybdenum, copper, tungsten, gold and antimony, in particular zinc, rhenium, tin, and gold e.g. tin. The second metal may be deposited upon the support before or after the deposition of the first metal by any of the methods herein described but preferably the two metals are deposited upon the support simultaneously. The second metal is preferably present, at least in part, in elemental form.

The preferred combination of metals for the dehydrogenation catalyst are selected from the list including platinum-rhenium, palladium-rhenium, platinum-zinc, palladium-zinc platinum-tin, palladium-tin, palladium-gold and platinum-gold, especially platinum-zinc, palladium-zinc, platinum-tin, and palladium-tin e.g. platinum-tin.

Most preferably the support is oxidic and especially selected from the list, alumina, silica, silicalite, ceria and titania, especially silica and silicalite.

Usually at least 0.1% (by weight of support) e.g. 0.1–10% such as 0.1–1% of at least one transition metal is deposited upon the support. In catalysts containing at least one second metal at least 0.1% (by weight of support) e.g. 0.1–20% such as 0.1–2% of a second metal is additionally deposited upon the support.

In preferred embodiment of the invention the dehydrogenation catalyst comprises platinum deposited on an aluminosilicate molecular sieve as described in PCT patent application WO 9315835 which is hereby incorporated by reference.

Prior to the reaction the dehydrogenation catalysts are usually pretreated. The pretreatment usually comprises passing air over the catalyst bed at a temperature of 200–800° C. preferably 300–700° C. e.g. 400–600° C. and subsequent treatment with flowing hydrogen at 100–800° C. preferably 200–700° C. e.g. 400–600° C.

The product suspension may be withdrawn from the Fischer-Tropsch reactor system as described in WO 0138269 (PCT patent application number GB 0004444).

The liquid hydrocarbon products may be separated from the particulate Fischer-Tropsch catalyst and purified also as described in WO 0138269 (PCT patent application number GB 0004444).

The liquid hydrocarbon products from the Fischer-Tropsch reaction may be fed to a hydrocracking and/or isomerisation stage also as described in described in WO 0138269 (PCT patent application number GB 0004444).

BRIEF DESCRIPTION OF THE DRAWINGS

The invention will now be illustrated with the aid of FIG. 1 which shows a reactor scheme for carrying out the invention.

DETAILED DESCRIPTION OF PREFERRED EMBODIMENTS

Figure 1:
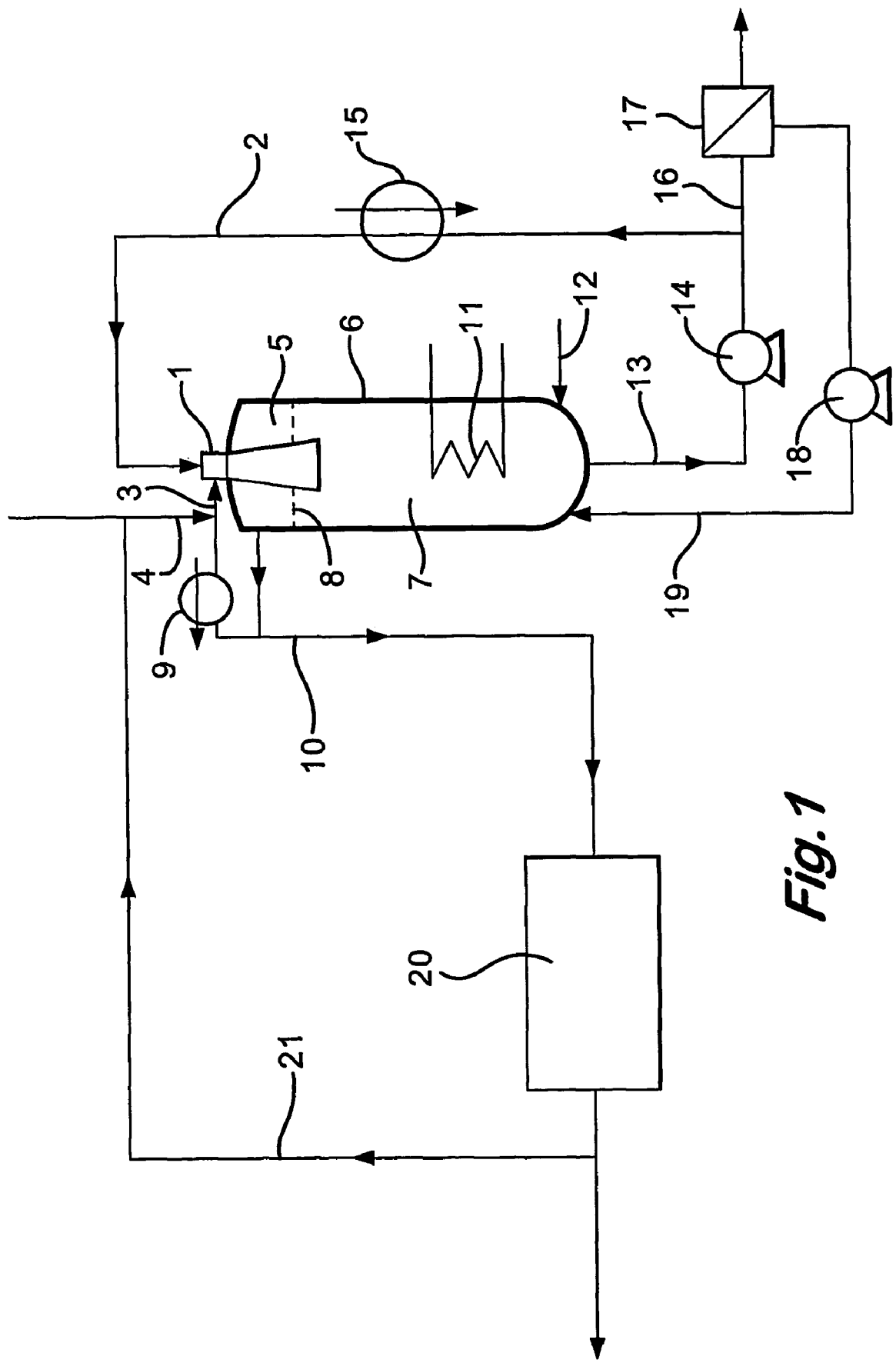

A suspension of a catalyst in a liquid medium is recycled to an injector-mixing nozzle (1) via a line (2). Through one or more openings in the side wall of the injector-mixing nozzle (1) the suspension draws in a gaseous reactant stream comprising synthesis gas, which is introduced into the injector-mixing nozzle (1) via a line (3). Fresh synthesis gas produced by the synthesis gas production stage (not shown) is introduced via a line (4) into a line (3) through which unconverted synthesis gas is recycled from a gas cap (5) which is present in the upper part of a vessel (6) the lower part of which contains a suspension (7) of the catalyst in a mixture of the liquid medium and liquid hydrocarbon products. A dotted line (8) in the Figure denotes the upper level of the suspension (7) in the vessel (6).

By means of cooling in a heat exchanger (9) the gas mixture passing through the line (3) is maintained at the correct operating temperature. Suitably, the heat exchanger (9) is a condenser having a water trap for removing water by-product from the system.

Optionally a heat exchanger (11) e.g. cooling tubes is provided below the level of the suspension (7) in the vessel (6) to assist in removing the exothermic heat of reaction.

Via a line (13) the product suspension (7) comprising catalyst suspended in the liquid medium and liquid hydrocarbon products is withdrawn from the bottom of the vessel (6) and at least a portion of the suspension is recycled to the injector-mixing nozzle (1) by means of pump (14) and the line (2). By means of cooling in a heat exchanger (15) the recycled suspension in the line (2) is maintained at the correct operating temperature.

The heat removed from the suspension via heat exchanger (15) and preferably heat exchanger (11) is used to heat the dehydrogenation unit (20).

Via a line (16) a portion of the suspension (7) is withdrawn from the system. By a suitable separation means (17), e.g. a hydrocyclone, filter, gravity separator or magnetic separator, or alternatively, by distillation, the liquid medium and liquid hydrocarbon products may be separated from the suspended catalyst. Separated catalyst may be returned to the vessel (6) as a slurry via a slurry pump (18) and a line (19). The separated liquid medium and liquid hydrocarbon products may be passed from the separation means (17) to a purification zone (not shown).

A gaseous stream comprising gaseous hydrocarbon products and unconverted synthesis gas is withdrawn from the gaseous recycle stream (3), passed to the dehydrogenation unit (20) via a line (10) wherein the gaseous stream is converted to olefins. At least a portion of the olefins are fed back into line (4) via line (21).

The invention claimed is:

1. A process for the conversion of synthesis gas to hydrocarbons comprising contacting the synthesis gas at elevated temperature and pressure with a suspension of a particulate Fischer-Tropsch catalyst in a liquid medium in a Fischer-Tropsch reactor system comprising at least one high shear mixing zone and a reactor vessel wherein the process comprises:
   a) passing the suspension through the high shear mixing zone(s) where the synthesis gas is mixed with the suspension;
   b) discharging a mixture comprising the synthesis gas and the suspension from the high shear mixing zone(s) into the reactor vessel;
   c) in the reactor vessel, converting the synthesis gas to hydrocarbons comprising gaseous and liquid hydrocarbons to form a product suspension comprising the catalyst suspended in the liquid medium and the liquid hydrocarbons;
   d) in a gas separation zone, separating a gaseous phase comprising saturated gaseous hydrocarbons from the product suspension;
   e) passing at least a portion of said separated gaseous phase to a dehydrogenation reactor where at least a portion of the saturated gaseous hydrocarbons are converted to unsaturated hydrocarbons; and
   f) recycling at least a portion of said unsaturated hydrocarbons back to the Fischer-Tropsch reactor system.

2. A process according to claim 1 wherein a stream comprising ethane, propane and butane is fed to the dehydrogenation reactor in addition to the separated gaseous phase.

3. A process according to claim 1 wherein the Fischer-Tropsch reactor system comprises at least one internal heat exchanger where coolant liquid is fed to the heat exchanger to remove exothermic heat of reaction from the system and wherein heat removed by the coolant liquid is then used to increase the temperature of the dehydrogenation reactor.

4. A process according to claim 1 wherein the Fischer-Tropsch reactor system comprises at least one external heat exchanger for cooling a recycle stream which is withdrawn from the reactor system and recycled wherein coolant liquid is fed to the external heat exchanger to remove exothermic heat of reaction from the system and wherein heat removed by the coolant liquid is then used to increase the temperature of the dehydrogenation reactor.

5. A process according to claim 2 wherein the reactor vessel is a tank reactor or a tubular loop reactor.

6. A process according to claim 2 wherein the high shear mixing zone(s) project through the walls of the reactor vessel such that the high shear mixing zone(s) discharges its contents into the reactor vessel.

7. A process according to claim 2 wherein the reactor system comprises up to 250 high shear mixing zones.

8. A process according to claim 2 wherein the high shear mixing zone(s) comprise an injector-mixing nozzle(s).

9. A process according to claim 8 wherein the injector mixing nozzle(s) is a venturi nozzle(s) or a gas blast nozzle (s).

10. A process according to claim 1 wherein the Fischer-Tropsch reaction is carried out at a temperature of 180–280° C. and at a pressure of 5–50 bar.

11. A process according to claim 1 wherein the particulate Fischer-Tropsch catalyst comprises cobalt supported upon zinc oxide.

12. A process according to claim 1 wherein the separated gaseous phase passed to the dehydrogenation reactor comprises vaporized low boiling liquid hydrocarbon products, and gaseous hydrocarbons having from 1 to 3 carbon atoms such as methane, ethane and propane.

13. A process according to claim 1 wherein the dehydrogenation process is carried out at a of temperature 300–700° C. and at a pressure of 0.1–10 bar.

14. A process according to claim 1 wherein the dehydrogenation reactor comprises a dehydrogenation catalyst.

15. A process according to claim 1 wherein the dehydrogenation catalyst comprises platinum supported on an aluminosilicate molecular sieve.

* * * * *